United States Patent
Ikuno et al.

[11] Patent Number: 5,980,103
[45] Date of Patent: *Nov. 9, 1999

[54] APPARATUS AND METHOD FOR TESTING THERMAL FATIGUE RESISTANCE

[75] Inventors: Hajime Ikuno; Masanao Hori, both of Aichi, Japan

[73] Assignee: Kabushiki Kaisha Toyota Chuo Kenkyusho, Aichi-ken, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/736,429

[22] Filed: Oct. 24, 1996

[30] Foreign Application Priority Data

Oct. 24, 1995 [JP] Japan .................................. 7-275460

[51] Int. Cl.$^6$ ...................................................... G01N 3/60
[52] U.S. Cl. .............................. 374/57; 374/5; 73/865.6
[58] Field of Search .......................... 374/57, 5; 73/865.6

[56] References Cited

U.S. PATENT DOCUMENTS

| | | | |
|---|---|---|---|
| 4,733,973 | 3/1988 | Machak et al. | 374/57 |
| 4,787,752 | 11/1988 | Fraser et al. | 374/57 |
| 4,793,716 | 12/1988 | Wei et al. | 374/57 |
| 4,807,247 | 2/1989 | Robbins, III | 374/57 |
| 4,817,447 | 4/1989 | Kashima et al. | 374/57 |
| 5,039,228 | 8/1991 | Chalmers | 374/57 |
| 5,294,199 | 3/1994 | Boersen et al. | 374/57 |

FOREIGN PATENT DOCUMENTS

| | | | |
|---|---|---|---|
| 60-33031 | 2/1985 | Japan . | |
| 0117127 | 6/1985 | Japan | 374/57 |
| 0198335 | 8/1990 | Japan | 374/57 |
| 403248035 | 11/1991 | Japan | 374/57 |
| 405164669 | 6/1993 | Japan | 374/57 |
| 7-20031 | 1/1995 | Japan . | |

*Primary Examiner*—Andrew Hirshfeld
*Attorney, Agent, or Firm*—Oblon, Spivak, McClelland, Maier & Neustadt, P.C.

[57] ABSTRACT

An apparatus and method for testing thermal fatigue resistance. The apparatus utilizes a unified heating device and cooling device so that the apparatus is smaller and simpler and a more even temperature distribution can be obtained. The apparatus has at least one gas duct facing the test unit and a device for supplying the duct with a compressed gas flow. A plurality of gas ducts may be used which face plural points on the test unit from plural directions. Thermocouples are placed on several points on the test unit and the temperatures of the points measured. Swift and precise testing of thermal fatigue resistance can be performed by a feedback control of each heating device based on the measured temperature. Thermal strains are caused in certain parts of the test unit due to differences of thermal expansion between members of the test unit.

16 Claims, 10 Drawing Sheets

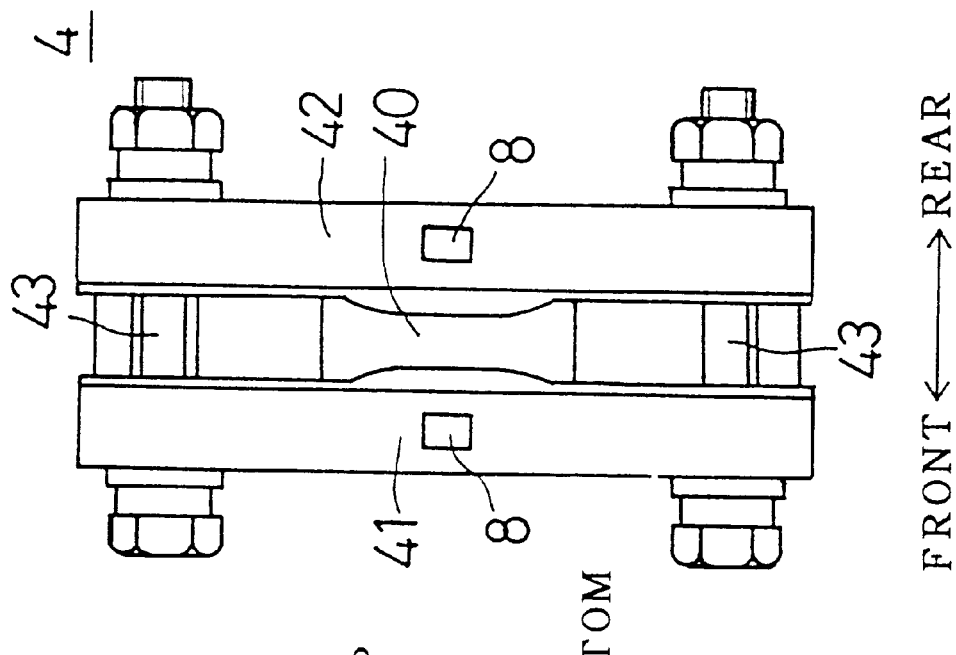
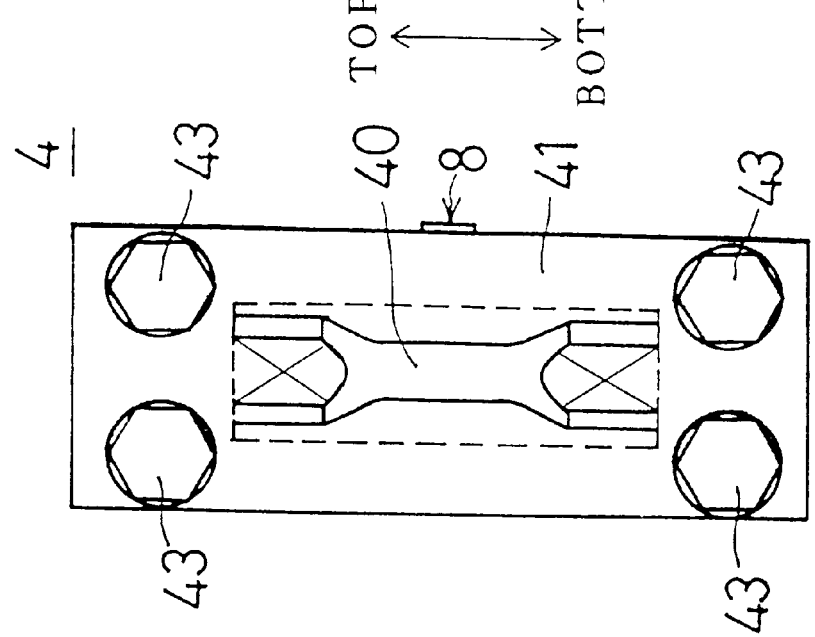
FIG. 2A
FIG. 2B

APPARATUS AND METHOD FOR TESTING THERMAL FATIGUE RESISTANCE

BACKGROUND OF THE INVENTION

1. Field of the Invention

This invention is related to an apparatus and a method for testing thermal fatigue resistance, and belongs to the engineering field of testing thermal fatigue resistance.

2. Description of the Related Art

A technique for testing thermal fatigue resistance is disclosed in Japanese Unexamined Patent Publication (KOKAI) No.7-020031. It is a testing technique in which a test piece is put between two pieces of a holder with thermal expansion coefficient different from the coefficient of the test piece, and the test unit consisting of the test piece and the holder is heated up and cooled down. The difference in the thermal expansion coefficient between the test piece and the holder is used to cause the required strain on the test piece, so that thermal fatigue test is performed.

In the testing technique described above, any actuators are not necessary to cause the mechanical strain in the test piece, so the technique has some advantage in the cost of the testing facility. The technique, however, was still to be improved because the facility was not compact enough nor simple enough, as it needed both means for heating and means for cooling separately. Also, heating and cooling of the whole test unit caused nonuniform temperature distribution due to difference of thermal capacity in every part of the test unit and made it difficult to give a required temperature distribution intentionally to the test piece.

Thus, the purpose of the invention is to provide an apparatus for testing thermal fatigue resistance which has unified means for heating and cooling and can provide a smaller and simpler set up, and to provide a method for testing thermal fatigue resistance by which required temperature distribution on the test unit can be obtained intentionally.

SUMMARY OF THE INVENTION

To accomplish the purpose, the inventors have made the invention as follows.

The first aspect of the present invention is an apparatus for testing the thermal fatigue resistance which comprises:

at least one gas duct having heating means inside thereof and has a nozzle facing to a test unit;

an output control unit for controlling the output of said heating means;

compressed gas supplying means for supplying compressed gas to said gas duct; and a valve which opens and closes a channel of the gas to be supplied to said gas duct.

In the apparatus described above, as the gas duct to which the compressed gas is supplied has heating means, a hot gas flow and a cold gas flow from the gas duct can be selected by controlling the output of the heating means. Thus, the apparatus for testing thermal fatigue resistance can be made compact and simple, as heating means and cooling means are united in the gas duct in this aspect of the invention.

Examples of the compressed gas include air, nitrogen gas, inert gas and the like. Air is most suitable as an inexpensive and clean heating and cooling media. In case the test piece is easily oxidizable, it is preferred to use nitrogen gas or inert gas.

Any heating means which can heat the gas flow may be used. Electric heating means such as an electric heater whose output is controlled electrically is preferred. The use of the electric heating means enables the control of the temperature of the gas flow easily and precisely.

It is preferred that the apparatus has plural number of the above-mentioned gas ducts and that the nozzles of the gas ducts are facing the test unit from a multiple direction. With this configuration, it becomes possible to blow the gas flow on desired portions (parts) of the test unit at a desired temperature. Thus, the desired temperature distribution is provided on the test unit.

The above-mentioned test units include test pieces of every kind of materials, electronic cells such as semiconductor tips, electronic parts provided with number of electronic cells, large parts with complicated figures and so on, i.e., anything which is subjected to any damage or degrading by thermal cycles. Using the apparatus, desired thermal cycles may be applied to a part (portion) or the whole of these test pieces. In case that the test piece is made of a single material, thermal strain is caused from the given temperature distribution. Also, in case the test piece is made of plural materials with different thermal expansion coefficients, mere heating or cooling to a certain temperature can cause thermal strain due to the difference of thermal expansion. Thus, repetitive heating and cooling would repetitively give thermal strain to the test unit, so that the apparatus is effective for evaluating thermal fatigue resistance of the test units.

The second aspect of the present invention is the apparatus which comprises, in addition to the construction of above-mentioned first aspect:

a temperature sensor placed on of said test unit and/or in the vicinity said nozzle of said gas duct;

temperature measuring means for measuring temperature at a portion where said sensor is placed based on a signal from said temperature sensor and generating a measured temperature signal; and controlling means for generating a control signal to control the output of said heating means to a proper level based on said measured temperature signal.

Using the apparatus, the temperatures of desired portions (parts) are measured by the thermal sensor and temperature measuring means, and then controlling means operates based on the measured temperature signals so that the temperature of the gas flow from each gas duct is controlled individually by the output control unit and/or valve driving means. Thus, the apparatus of this aspect can effectively work on temperature control with improved precision and within reduced time, because feedback control is done by sensor/controller system.

The third aspect of the present invention is an apparatus of the first aspect, in which said test unit comprises a test piece and a holder which is made of material with thermal expansion coefficient different from that of the test piece, and the test piece is fixed to the holder so that thermal expansion of the test piece is restricted by the holder.

Using the apparatus of the third aspect, thermal strain is caused in the test piece by the holder by heating and cooling each of the holder and the test piece, because the thermal expansion coefficients are different between the holder and the test piece. Thus, the apparatus does not need any actuator to give stress to the test piece in thermal fatigue resistance tests, so it does not cost much and it is simple and also reliable.

It is preferable that at least one of said test piece and said holder is equipped with at least one strain gauge. With this configuration, the life limit to damage of the test piece can be obtained from the change of the output of the strain gauge.

The fourth aspect of the present invention is a method for testing thermal fatigue resistance, wherein a cold gas flow and a hot gas flow are blown from at least one nozzle of the gas duct to at least one part of the test unit alternately, so that thermal cycles are given to the test unit. In this method, the temperature of the gas flow from each gas duct is controlled individually.

With this method, the cold or hot gas flow of desired temperature can be blown to the desired portions (parts) of the test unit, because the temperature of the gas flow is controlled individually and the gas flow is blown from at least one nozzle of the gas duct. Thus, using the method, desired distribution of temperature is effectively obtained on the test unit. Of course, it is also possible to give uniform distribution of temperature on the test unit. Besides, thermal strain can be effectively controlled on the desired portions (parts) of the test unit by giving desired distribution of the temperature.

The air, nitrogen gas and inert gas can be used for the above-mentioned gas. The air is most suitable as cheap and clean heating and cooling media. In case the test unit is easily oxidized, use of nitrogen gas or inert gas is desirable.

The fifth aspect of the present invention is a method of the fourth aspect in which at least one of the temperature of desired portion (part) of said test unit and the temperature of said gas flow at the nozzle of the gas duct is measured, so that the temperature of the gas flow is controlled based on the result of the measurement.

In this method, measurement and control are performed to provide a sensor/controller system, which makes it possible to utilize many kinds of control technique such as feedback control. Thus, using the method will make it possible to perform temperature control and strain control more rapidly and more precisely.

The sixth aspect of the present invention is a method of the above-mentioned fifth aspect in which the hot gas flow is the gas flow which is heated or kept at a certain temperature by heating means, and the cold gas flow is the gas flow which is cooled or kept at certain temperature by air-cooling or auxiliary heating by heating means, said heating means is an electric heating means in which the output is controlled electrically; and said temperature control is PID control which is performed by controlling the output of the electric heating means by the following numerical formulas:

$$V \text{out} = \{K \cdot Th(t)\}^\beta$$

$$Th(t) = 100/PB \cdot \{e(t) - 1/TI \cdot \int e \, dt + TD \cdot de(t)/dt\}$$

wherein,
V out : heater control signal (by voltage or by current)
Th(t): controlled heater temperature
t: time β: a constant index
PB: proportional band (%)
TI: time for integration
TD: time for differentiation
e(t): deviation of controlled temperature of the gas flow, i.e., e(t)=SV−PT(t)
SV: target temperature of the gas flow
PV(t): measured temperature of the gas flow This method makes it possible to perform electric control of temperature of the gas flow more swiftly and more easily, because electrical heating means such as an electric heater is used to heat up the gas flow. Moreover, swift and precise thermal control is performed with such a simple control logic, because the output of the heater as heating means is controlled by PID control which follows the above formula in which control signal/temperature characteristics of the heater are considered. Thus, using this method makes it effectively easier to perform swift and precise thermal control and strain control.

Further, it is preferable to keep Vout constant compulsorily for a certain duration in the beginning of heating and cooling. That effectively shortens the delay in thermal control in the beginning of heating and cooling, so that thermal fatigue resistance test would be performed swiftly.

The seventh aspect of the present invention is the method of the above-mentioned sixth aspect in which said gas flow is the hot gas flow and the cold gas flow which are blown alternately by the following numeric formulas;

$$SV(1) = SV0$$

$$SV(i) = SV(i-1) + Etp(i-1)$$

wherein,
SV(i): target temperature of the gas flow of the i-th cycle
SV0: initial target temperature
Etp (i−1): thermal deviation of the test unit at (i−1)th cycle,
Etp (i−1)=SVtp−PVtp (i)
SVtp: target temperature of the test unit
PVtp (i−1) : measured temperature of the test unit This method effectively makes it possible to perform precise thermal control by correcting temperature variations caused with the passage of time, because the target temperature is corrected in every cycle based on the deviation of the measured temperature of the test unit from the former target temperature.

BRIEF DESCRIPTION OF THE DRAWINGS

The present invention will be more fully understood with reference to the following description and the appended drawings, wherein like elements are designated by the same reference numerals as in the description. In the drawings:

FIG. 2A shows the front view of the test unit of the embodiment, and FIG. 2B shows the side view of the same.

DETAILED DESCRIPTION OF THE PREFERRED EMBODIMENT (Embodiment 1)

1. Apparatus for Testing Thermal Fatigue Resistance

Figure 1:
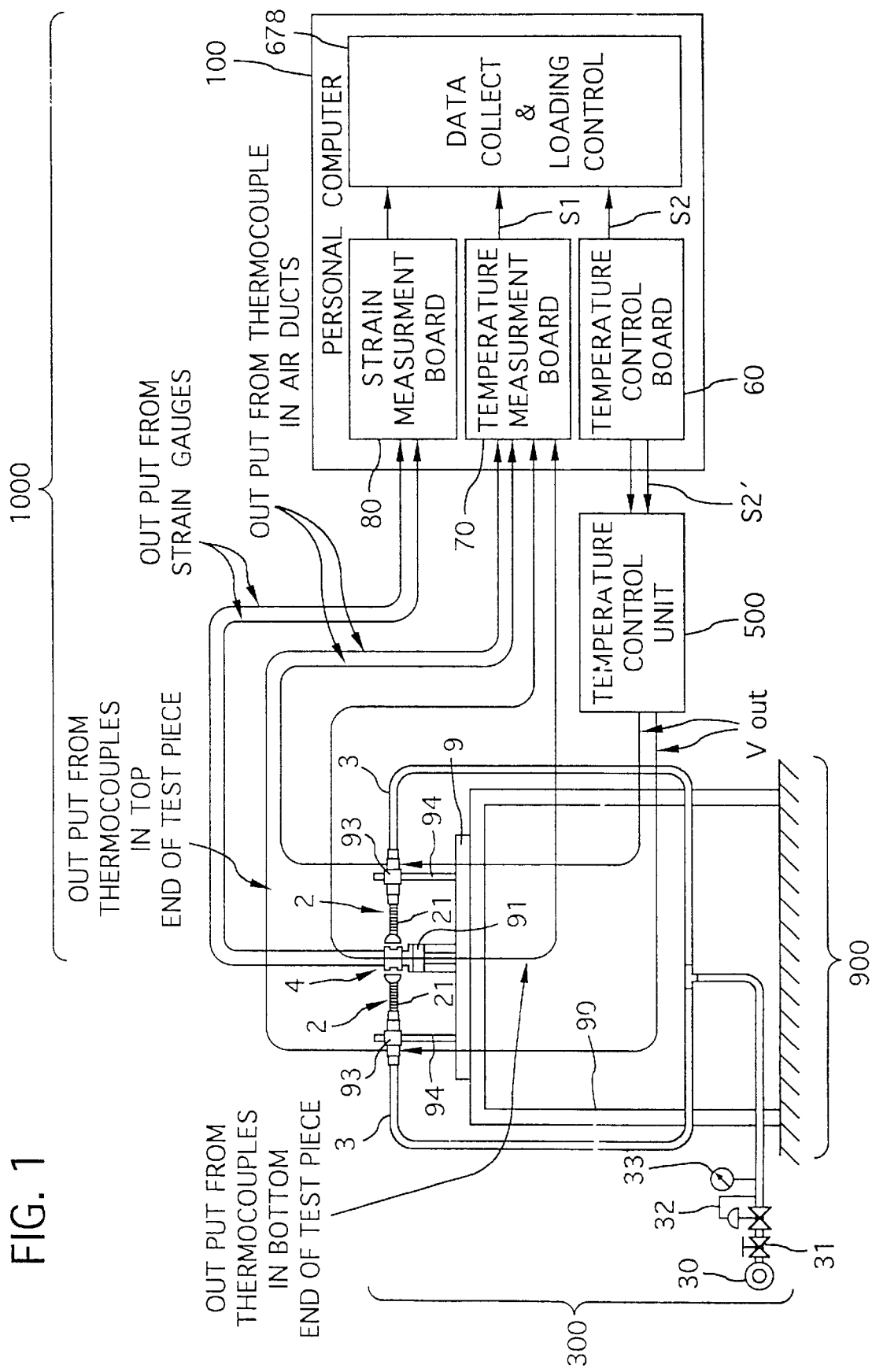
FIG. 1 shows the whole configuration of an apparatus for thermal fatigue resistance testing as an embodiment of the present invention.

An apparatus for thermal fatigue testing as an embodiment of the present invention, as shown in FIG. 1, comprises a base unit 900 fixing a test unit 4 and air ducts 1, 2, compressed gas supplying means 300 for supplying the air duct 1, 2 with compressed air, and a temperature control unit 500 and a personal computer 100 as a sensing and controlling unit.

(1) Test Unit (Test Piece & Holder)

As shown in FIGS. 2A and 2B, the test unit 4 comprises a test piece 40, two parts of holders 41, 42 holding the test piece 40 from the front and the rear, and four (or two) bolts and nuts 43 fixing the test piece and the holders 41, 42 to each other at their both top end and bottom end.

The test piece 40 has a middle portion of circular cross section with a constant sectional area similarly to a test piece used in a tensile test. The test piece also has at its upper and lower ends thick portions with parallel planes to be attached to inside surfaces of the holders 41, 42. The surfaces between the middle portions and the thick portions are formed smoothly to prevent stress concentration.

On the other hand, the holders 41, 42 are made of blocks of the same material and dimension. The coefficient of linear thermal expansion due to temperature change is different between the holder and the test piece. Each of holders 41, 42 has a shape of a rectangular solid and has no windows except for four bolt holes. Four strain gauges 8 are placed on the central portions of the front and rear sides of the holders 41, 42, and other strain gauges may be placed on the test piece 40 if necessary.

On the inside surfaces of the holders 41, 42 at the upper and lower ends thereof there are provided ridges and grooves alternately and transversely to the longitudinal direction thereof. The inside surfaces with ridges and grooves are pressed into parallel planes at the both ends of the test piece 40, so that the test piece 40 and the holders 41, 42 are fixed firmly to each other at the both ends by the ridges and grooves. The holders 41, 42 holds the test piece tightly at the both ends by bolts and nuts 43 through the both end parts of the holders 41, 42. Each of the bolts and nuts 43 is compressed through a conical spring washers against the outsides of the holders 41, 42.

The Japanese Unexamined Patent Publication (KOKAI) No. 7-20031 should be referred to for further understanding of the test unit 4 comprising the test piece 40, the holders 41, 42, and the bolts and nuts 43. The publication shows a test unit similar to the test unit 4 in detail.

(2) Base Unit

A base unit 900, also shown in FIG. 1, has a horizontal flat table (as a test table) 9 supported by frame 90 on the floor. The test unit 4 is fixed on a supporter block 91 on the center of the flat table 9. The supporter block 91 fixes the test unit 4 from both sides by a sort of a vise using nails 92 made of ceramic plates (see FIG. 4). Even though the ceramic nails 92 are attached to the test unit 4, the nails 92 makes little thermal disturbance by conduction of heat, because the thermal conductivity of the nails 92 is very low. The air ducts 1, 2 are fixed to the table 9 with their axis on the level through poles 94 and clamps 93. The nozzles of the air ducts 1, 2 (1 not shown in FIG. 1) are individually facing to the test unit 4.

Figure 3:
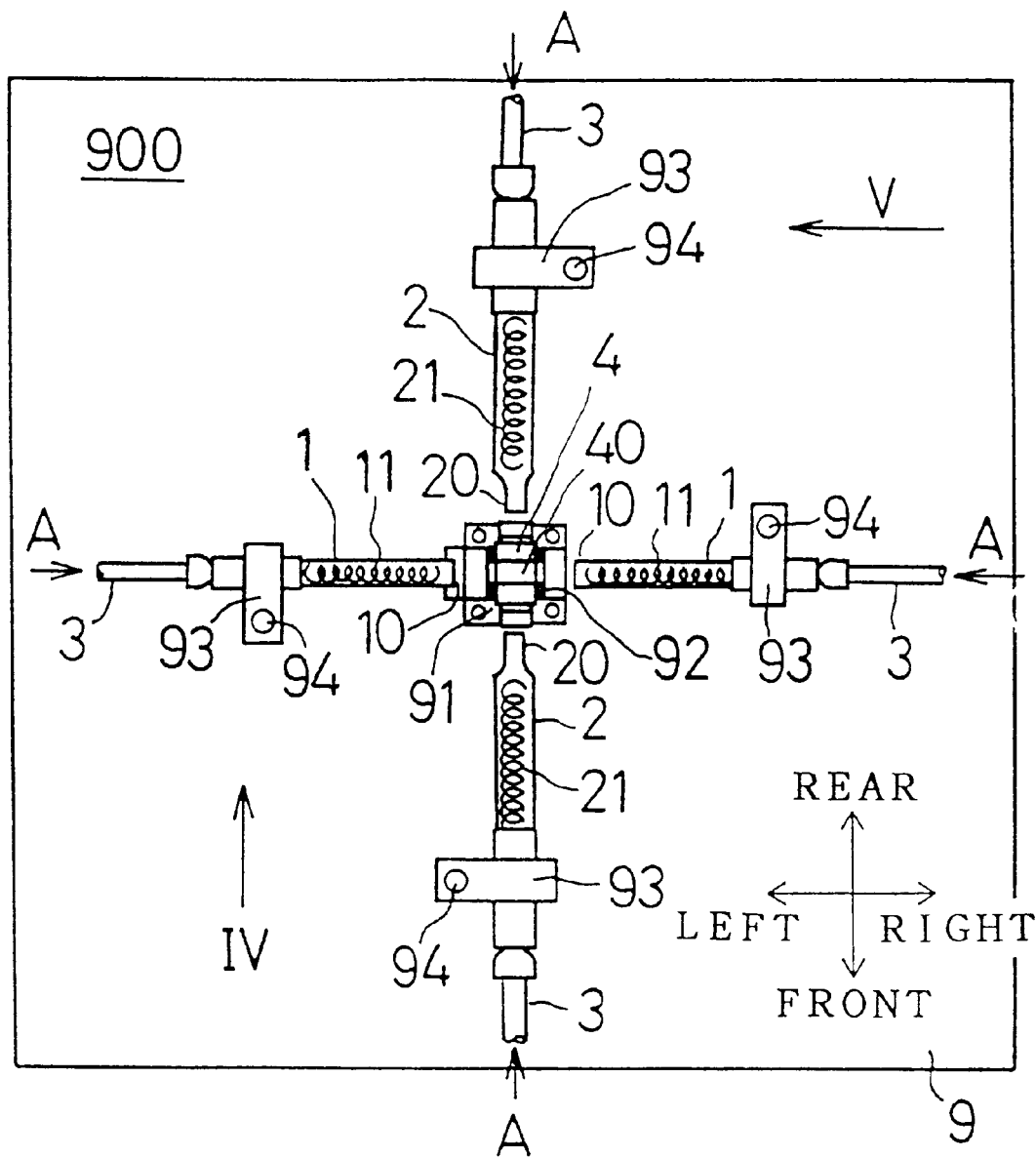
FIG. 3 is the plain view showing the arrangement of the test unit and the gas ducts of the embodiment.

That is to say, as shown in FIG. 3, air ducts 1 are placed to blow compressed air flow A from the right and the left of the test unit 4 standing on the center of the table 9, and air ducts 2 are placed to blow the compressed air flow A from the front and the rear of the test unit 4.

Figure 4:
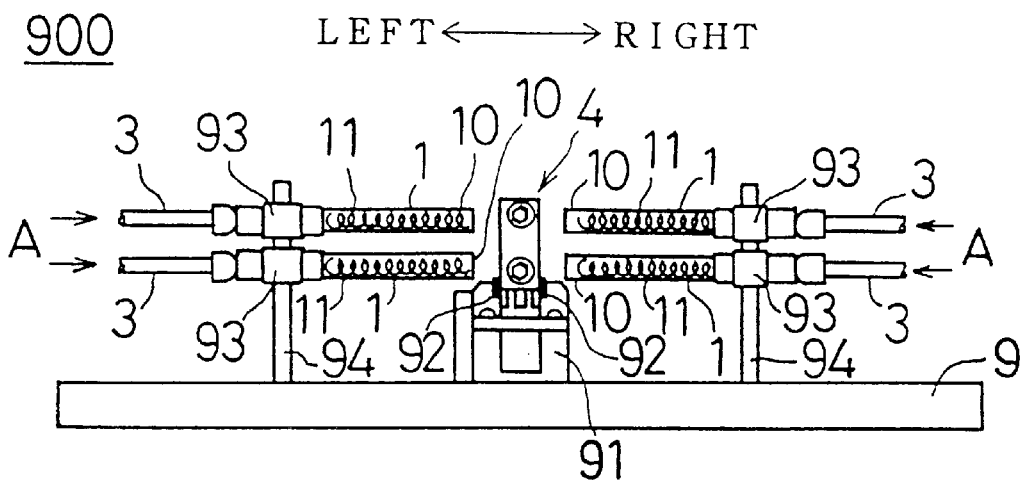
FIG. 4 is the front view showing the arrangement of the test unit and the gas ducts of the embodiment.

As shown in FIG. 4, there are four air ducts 1 each pair of which are placed over one other. Air hoses 3 from a compressed air source (not shown) are connected to the rear ends of the air ducts 1 to supply each air duct 1 with the compressed air A. An electric heater (air heater) 11 made of heating wire coil is provided in each of the air ducts 1, and can heat up the compressed air flow A. Each of the air ducts 1 has an open end (a nozzle) 10 facing the test unit 4, so that the compressed air flow A can blow directly against the test piece 40 from both sides of the test unit 4.

Figure 5:
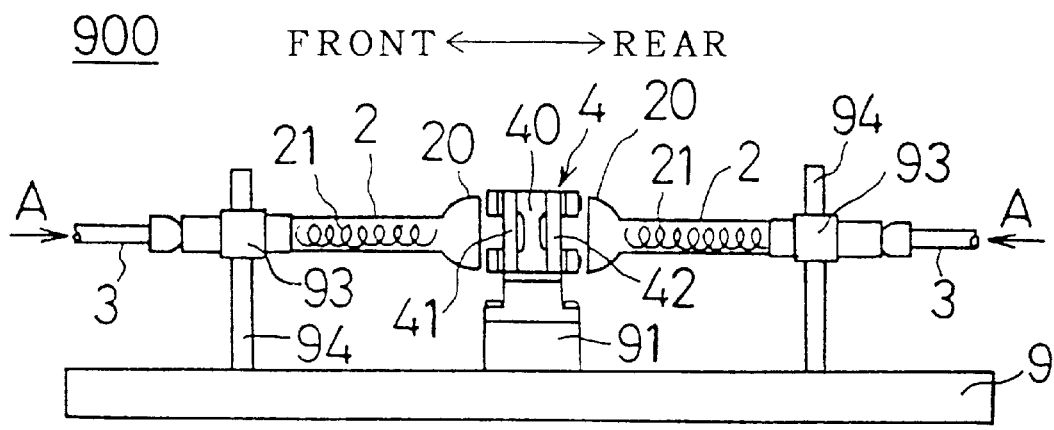
FIG. 5 is the side view showing the arrangement of the test unit and the gas ducts of the embodiment.

As shown in FIG. 5, the two air ducts 2 are fixed on opposite side of the test unit 4 facing each other. Similarly to the air ducts 1, air hoses 3 from a compressed air source (not shown) are connected to the rear ends of the air ducts 2 to supply each air duct 2 with compressed air A. An electric heater (air heater) 21 made of heating wire coil is provided in each of the air ducts 2, and can heat up the compressed air flow A. Each of the air ducts 2 has its open end (nozzle) 20 expanded in the shape of an opened fan, so that the compressed air flow A can blow directly against holders 41, 42 only from the front and the rear of the test unit 4.

(3) Compressed Air Supplying Means

Figure 6:
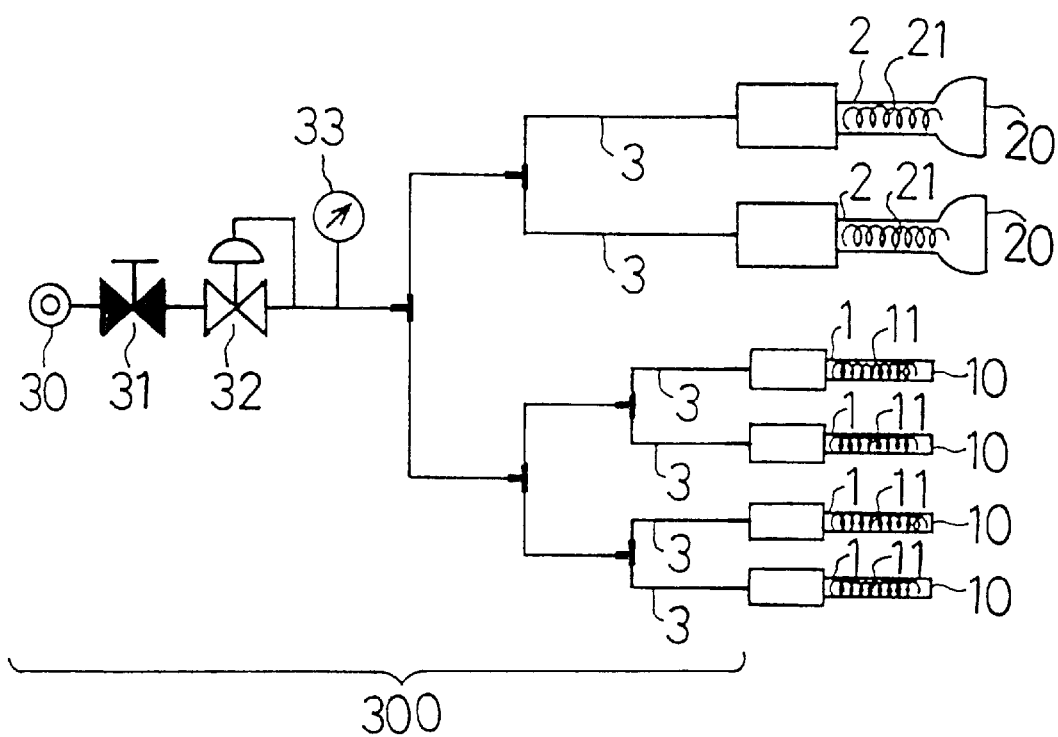
FIG. 6 is the system chart showing the arrangement of compressed gas supplying means of the embodiment.

As shown again in FIG. 1, compressed air supplying means 300 comprises the source of compressed air 30, the air hose 3 connected individually to the every air duct 1, 2, and a valve 31, a pressure control valve 32 and a pressure meter 33 which are inserted in the pipe which connects the source 30 and the air ducts 1, 2. As shown in FIG. 6, the compressed air A supplied from the source 30 is delivered to every air duct 1, 2 through its hose after the pressure is regulated at an appropriate value by the pressure control valve 32.

A compressed air pipe from a compressor settled in the facility was used as the source 30 of compressed air A. There may be a little pulsing fluctuation in supplying pressure of the source 30, but that causes no problem.

(4) Sensor/Controller System

In the apparatus for thermal fatigue testing, sensor/controller system 1000 comprises thermal sensors and strain sensors, a personal computer, temperature control unit 500 and the electric heaters 11, 21 (see FIG. 1).

(5) Thermal Sensor System

Figure 7:
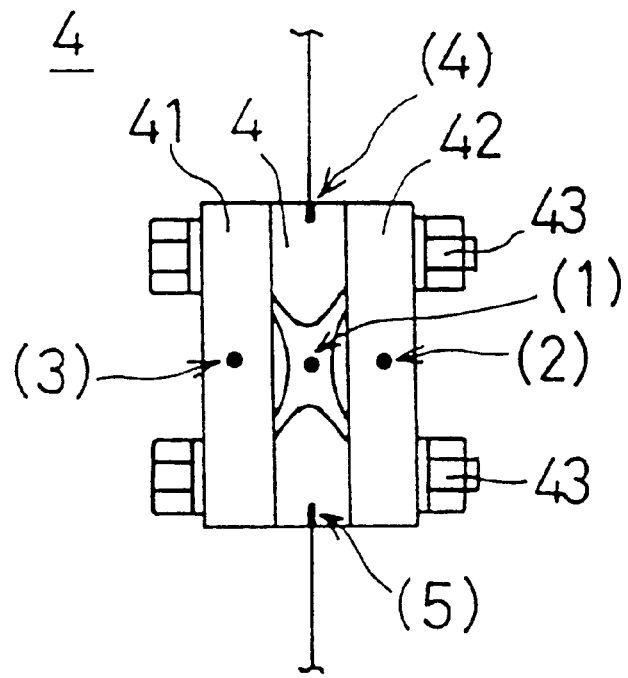
FIG. 7 shows the positions of the thermocouples placed on the test unit of the embodiment.

As a thermal sensor system, CA(chromel/almel) thermocouples are placed on eleven points, i.e., five points on the test unit 4 and six points at the open end or the nozzle 10, 20 of the air ducts 1, 2. On the test unit 4, as shown in FIG. 7, one thermocouple (1) is placed on the surface of the middle portion of the test piece 40, two thermocouples (4), (5) are individually placed in holes at the upper and lower ends of the test piece 40, and two thermocouples (2), (3) are individually placed on the surfaces on one side of the holders 41, 42. On the other hand, the thermocouples (6)–(11) are placed inside of the open ends or the nozzles 10, 20 of the air ducts 1, 2, as shown in FIG. 8, and the temperature of the air flow is measured in the open ends or the nozzles 10, 20.

Figure 8:
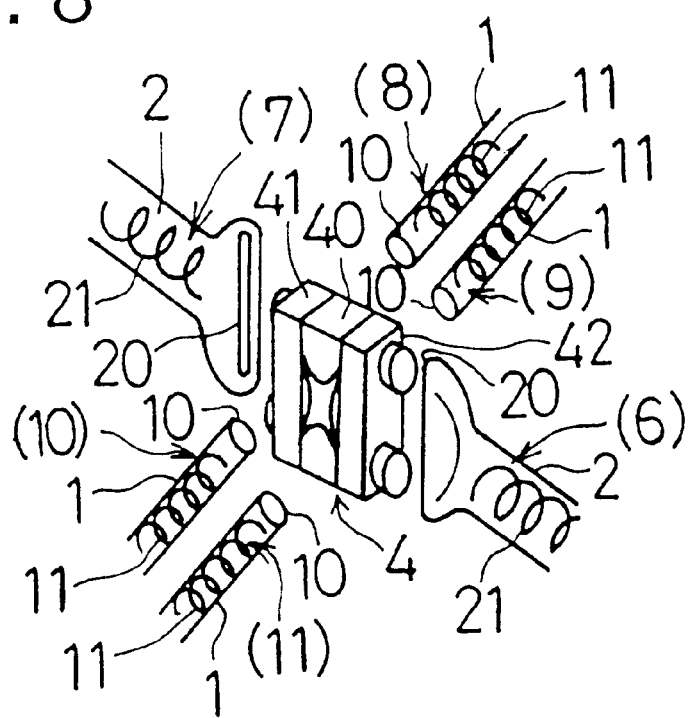
FIG. 8 is the perspective view showing the positions of the thermocouples placed in the gas ducts of the embodiment.

As shown clearly in FIG. 8, the open ends 10 of the four air ducts 1 directly face to the test piece 40 so as to send hot air flow and cold air flow to the thick end portions of the test piece 40. Thus, the middle portion of the test piece 40 to be tested is not directly blown in the air flow, and is heated and cooled by heat conduction from the end portions. That is because, if the middle portion of the test piece is blown directly, the temperature of the middle portion would change rapidly with the change of the temperature of the hot and cold air flow from the air ducts 1 as the middle portion has a relatively small diameter and a small heat capacity. In case the test piece 40 is made of metallic material, the heat conductivity of the test piece 40 is so high that the temperature distribution in the middle portion (the tested part) can be very uniform. In this way, high precision can be achieved in thermal fatigue test.

The air ducts 1 may be placed in a manner to directly face the middle portion of the test piece 40, only if it is certain that the temperature of the air flow from the air ducts 1, 2 are controlled precisely and stably, and if the heat capacity of the middle portion is not much smaller than that of the end portions. Or else, four air ducts 1 can be replaced with two air ducts just like the air ducts 2.

On the other hand, the open ends 20 of the two air ducts 2 face the holders 41, 42, so that the holders 41, 42 are directly blown by the hot air flow and the cold air flow. For that reason, test piece 40 is not heated nor cooled so directly by the hot or cold air flow from the air ducts 2.

Therefore, the temperature of the test piece 40 and the temperature of the holders 41, 42 can be controlled independently by giving different temperature to the air flow from the air ducts 1 and the air flow from air ducts 2. Hence, it is also possible to control the temperature and the tension strain (or compression strain) of the test piece 40 independently.

By the way, each of the output voltages from the eleven thermocouples (1)–(11) placed as mentioned above is, as shown in FIG. 1 and FIG. 9, led into a temperature measurement board 70 in the personal computer 100 via sensor leadwire (extension leadwire of the thermocouples). The temperature measurement board 70 is equipped with A/D converters for converting each of the output voltages into digital signals, a circuit for room temperature compensation, and another circuit for compensating the non-linearity of the outputs of the thermocouples. With the temperature measurement board 70 thus constructed, it is possible to perform precise measurement of temperature and output as digital signals measured temperature signals S1 at every point where each of the thermocouples is placed.

(6) Strain Sensor System

The holders 41, 42 are equipped with four strain gauges 8 on the side surfaces as the strain sensors (see FIGS. 2A and 2B). The output voltage of each strain gauge is, as shown again in FIG. 1 and FIG. 9, led to a strain measurement board 80 in the personal computer 100 via sensor leadwire.

The strain measurement board 80 is equipped with a relay circuit for switching to each strain gauge 8, a bridge circuit for the strain gauges 8, a power source circuit for the bridge circuit, and A/D converters for converting each of output from the bridge circuit into digital signals. In case that the board 80 can be equipped with the bridge circuits as many as the strain gauges 8, the above-mentioned relay circuit is not necessary. With this strain measurement board 80, it is possible to output as digital signals measured strain signals at every point where each of the strain gauges 8 are placed.

By the way, strain caused in the test piece 40 depends on the thermal expansion characteristics and the stress/strain characteristics of the test piece 40 in the thermal fatigue test of the embodiment. For that reason, in case of testing materials among which these characteristics are similar to each other, it is not necessary to place a strain gauge on the middle portion (the tested portion) of every test piece 40 to measure the strain on the test piece 40. However, sensors such as strain gauges and thermocouples may be placed on any portions of the test piece as far as they are necessary according to the aims or conditions of the tests.

Further, stress and strain in the test piece 40 can be precisely estimated or calculated, if compensations are done on such parameter as deviation of sensed strain and deviation of gauge ratios due to the temperature of the strain gauges 8 based on the data of temperature and strain measured as mentioned above, and on thermal dependency of the elasticity of the material forming the holders 41, 42 and so forth. The calculations for the compensation may be done not only in real time in the testing, but also they can be done by a personal computer or the like using data memorized on some memory media after the testing.

(7) Data Collection and Displaying the Data

The measured temperature signals S1 and measured strain signals mentioned above are input into the mother board 678 every second and stored in a RAM. Simultaneously, major signals are displayed on the display (not shown) appended to the personal computer 100. Thus, test engineers can monitor the temperature and strain of some position and the history of the same on the display.

(8) Temperature Control System

Figure 9:
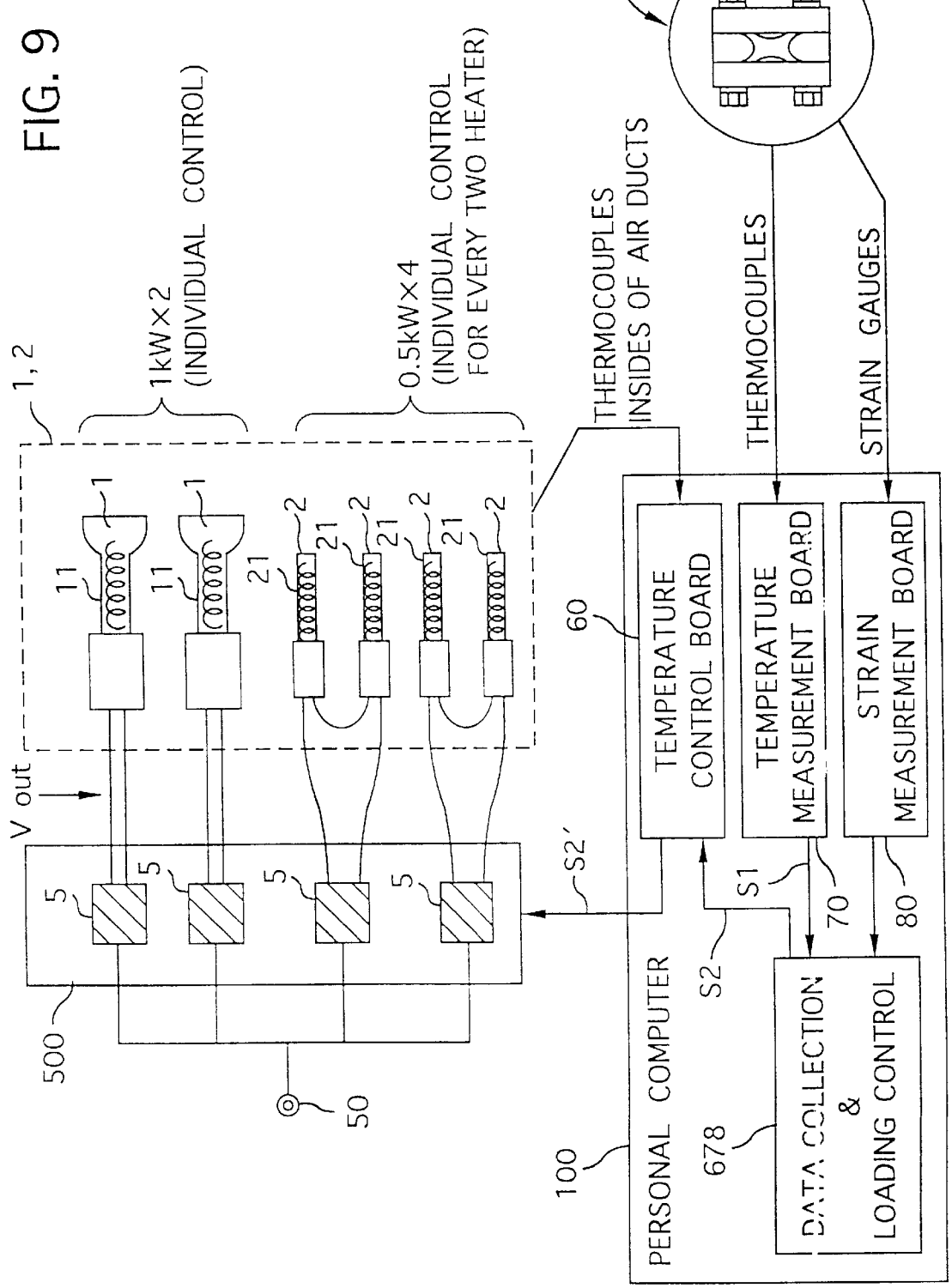
FIG. 9 is the system chart showing the arrangement of the sensor/controller system of the embodiment.

In the apparatus for testing thermal fatigue resistance of the embodiment, as shown in FIG. 9, appropriate digital control signals S2 for four systems are derived from a CPU as means for controlling on the mother board 678 which processes the above-mentioned measured temperature signals S1. Each of digital control signals S2 is transformed to analog voltage signals S2' by the temperature control board 60 equipped with D/A converters. The analog control signals S2' are output from the personal computer 100.

Each of the control signals S2' is input to the temperature control unit 500 and controls individually four voltage control units 5 placed on the temperature control unit 500. Every voltage control unit 5 is equipped with a power transistor driven with electric power supplied by the electric power source 50. Each of the voltage control units 5 controls voltage Vout applied to the air ducts 1, 2 via leadenness based on each of the control signals S2'.

The two air ducts 1 include individual electric heaters 11 with a standard output of 1 kW, and every electric heater is supplied with electric power from one of the voltage control unit 5. On the other hand, the four air ducts 2 include individual electric heaters 21 with a standard output of 0.5 kW, and pair of electric heaters of the air ducts 2 are connected in series. One of the voltage control units 5 is equipped for the every two electric heaters and supplies electric power. (Each of the electric heaters 11, 21 are combined to each other of same heat output by checking the heater output in advance.)

Thus, the electric heaters 11 of the air ducts 1 and the electric heaters 21 of the pairs of air ducts 2 are controlled independently by the voltage control units 5. For that reason, the temperature of the holders 41, 42 blown by the air ducts 1 and the temperature of the test piece 40 blown by the air ducts 2 can be controlled independently.

2. Method for Testing Thermal Fatigue Resistance (Operation of the Apparatus) (1) Outline Method for testing thermal fatigue resistance as a preferred embodiment of the present invention is performed as follows using the apparatus for testing thermal fatigue resistance constructed as mentioned above (see FIG. 1).

What is important in the testing method is to cause strain in the test piece 40 again and again due to a difference between thermal expansion coefficients of the test piece 40 and the holders 41, 42 by blowing the hot air flow and the cold air flow alternately to the test piece 40 and the holders 41, 42 from the nozzle 10, 20 of the air ducts 1, 2 in the four directions. The method is characterized by individual temperature control of the air flow from each nozzle 10, 20.

That is to say, the temperatures of the three positions on the test piece 40 and the holders 41, 42 and the temperature of the air flow at each of nozzles 10, 20 are measured, so that temperature of the air flow from the air ducts 1, 2 are controlled based on the measurements. The hot air flow or above-mentioned air flow is the air flow heated by the electric heaters 11, 21.

The air flow speed and the flow rate in the air ducts 1 are equal to each other, and the same applies to the air ducts 2 because both of the air ducts 1, 2 are supplied with the compressed air A from the same compressed air source 30.

For that reason, swift control of heating and cooling can be performed simply by keeping the flow rate of the compressed air A at the constant value and controlling the output of the electric heaters 11, 21 (i.e., controlling the applied voltage).

(2) PID Control

The output control of the electric heaters 11, 21 is performed by a program installed in the CPU on the mother board 678 according to the following control algorithm.

That is to say, the applied voltage Vout to the electric heaters 11, 21 (determined by the control signal S2) is controlled by the following PID control algorithm based on the control deviation e(t) of temperature of the air flow.

$$Vout = \{K \cdot Th(t)\}^\beta$$

$$Th(t) = 100/PB \cdot \{e(t) + 1/TI \cdot \int e\,dt - TD \cdot de(t)/dt\}$$

wherein,

Vout: output voltage signal for heater control

Th(t): controlled heater temperature t: time β: a constant index

PB: proportional band (%)

TI: time for integration

TD time for differentiation e(t) deviation of controlled temperature of the air flow, i.e., e(t)=SV−PT(t)

SV: target temperature of the air flow

PV(t): measured temperature of the air flow

Here, the latter of above numeric formulas is a usual formula for PID feedback control, so that the control variable ( the target temperature ) Th(t) for the electric heater is determined by the latter formula. And the applied voltage Vout (i.e., S2) is set according to the first formula of the algorithm based on the control variable Th(t). By the way, the third term of the latter formula (the differential term) may be replaced by an imperfect differential term, so that it would hardly pick up noise element.

Figure 10:
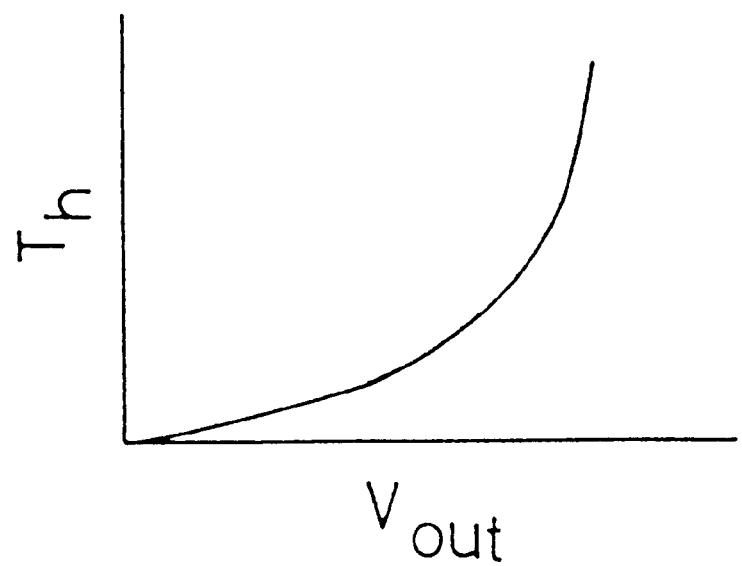
FIG. 10 is the graphic chart showing the relationship between the voltage applied to one of the heaters and the temperature of the gas flow.

According to preliminary experiments, there exists a nonlinear relationship as shown in FIG. 10 between the temperature Th(t) of the air flow from the air ducts 1, 2 and the applied voltage Vout. Then, taking account of the nonlinearlity, the relationship is approximated with an exponential function in the first formula. For that reason, the applied voltage Vout can be determined by the formula with Th(t) as target temperature. Incidentally, it is set so as β=0.87 in the embodiment.

The motherboard 678 is programmed to keep the applied voltage Vout forcibly to an appropriate constant value for a certain duration at the beginning of heating or at the beginning of cooling in the thermal fatigue test. In the embodiment, the applied voltage Vout is kept to be 1.5 V at the beginning of heating and to be 0 V at the beginning of cooling. That shortens the delay of temperature control at the beginning of heating and at the beginning of cooling, and then makes it possible to perform the thermal fatigue test swiftly. And besides, it is possible to slow down the pace of heating or cooling intentionally by coordinating the control parameters such as PB, TI, TD.

(3) Cycle Control

In the thermal fatigue testing, the cycles of heating and cooling are repeated for certain times. In the testing, the target temperature SV of the air flow from the air ducts 1, 2 are set according to the following way. That is, as shown in the following algorithm, it begins with a initial value SV0 predetermined by the preliminary testing. And then, from the second cycle, correction is added by taking the temperature deviation Etp (the target temperature—the measured temperature) at the middle portion of the test pieces 40 in the former cycle into consideration. In another way of the testing, the above-mentioned deviation Etp may be estimated by the temperature in the hole at the top end of the test piece 40 based on the relationship between the temperature of the middle portion of the test piece 40 and the temperature in the hole at the top end of the test piece 40. The relationship should be predetermined by preliminary testing in this case.

$$SV(1) = SV0$$

$$SV(i) = SV(i-1) + Etp(i-1)$$

wherein,

SV(i): target temperature of the air flow of i-th cycle

SV0: initial target temperature

Etp(i−1): thermal deviation of the test unit at (i−1)th cycle,

Etp (i−1)=SVtp−PVtp (i−1)

SVtp: target temperature of the test unit

PVtp (i−1): measured temperature of the test unit

Figure 11:
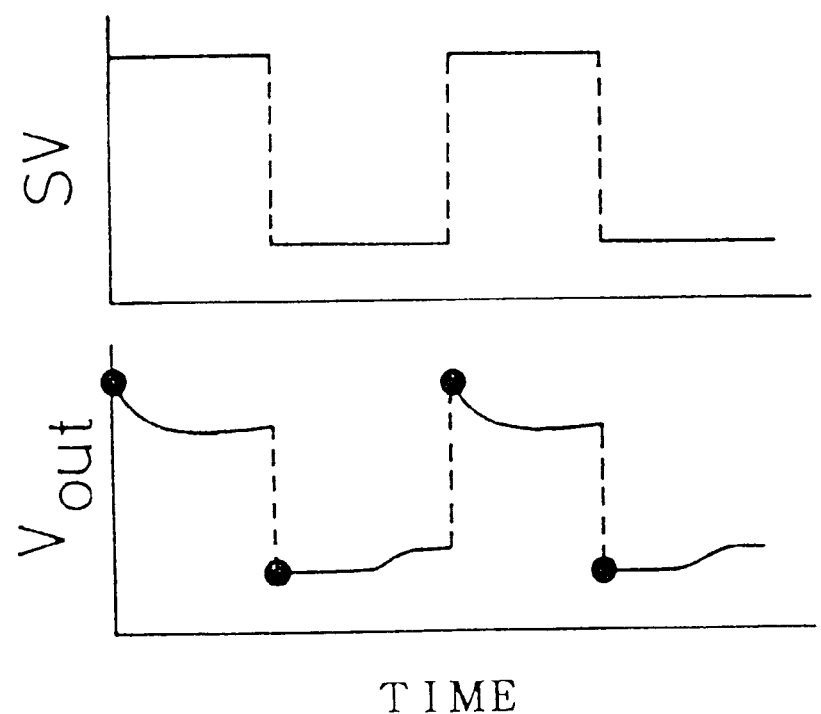
FIG. 11 is the time chart showing the target temperature of the gas flow and the applied voltage.

Precise range control of the upper limit and the lower limit of temperature of the test piece 40 can be performed with little influence of disturbances such as the room temperature, by correcting the target temperature SV of the air flow in every cycle according to the algorithm mentioned above. The precise control of the temperature is shown in FIG. 11.

In the method for thermal fatigue testing, the thermal strain (or the thermal stress) is caused by restricting the thermal expansion due to change of the temperature. For that reason, the controlling algorithm presented in the above-mentioned two numeric formulas makes it possible to repeat precisely the thermal cycles of the temperature of the test unit 4 (especially the test piece 40) in a certain range with good reproductivity. Thus, very precise thermal fatigue testing can be performed, because certain thermal strain is caused precisely in the test piece 40 and the holders 41, 42.

(4) Testing Result of the Embodiment No. 1

In the apparatus and the method for thermal fatigue testing mentioned above, the testing was performed with the target parameters set as shown in Table 1. In the testing, the flow rate of the compressed air A was kept at 320 l/min and the sampling interval and the controlling interval were 1 second.

TABLE 1

| | Target temperature of the Air Flow SV | Duration | Temperature of the Test Unit |
|---|---|---|---|
| Heat | 240° C. | 120 sec. | 200° C. |
| Cool | 50° C. | 180 sec. | 50° C. |

Figure 12:
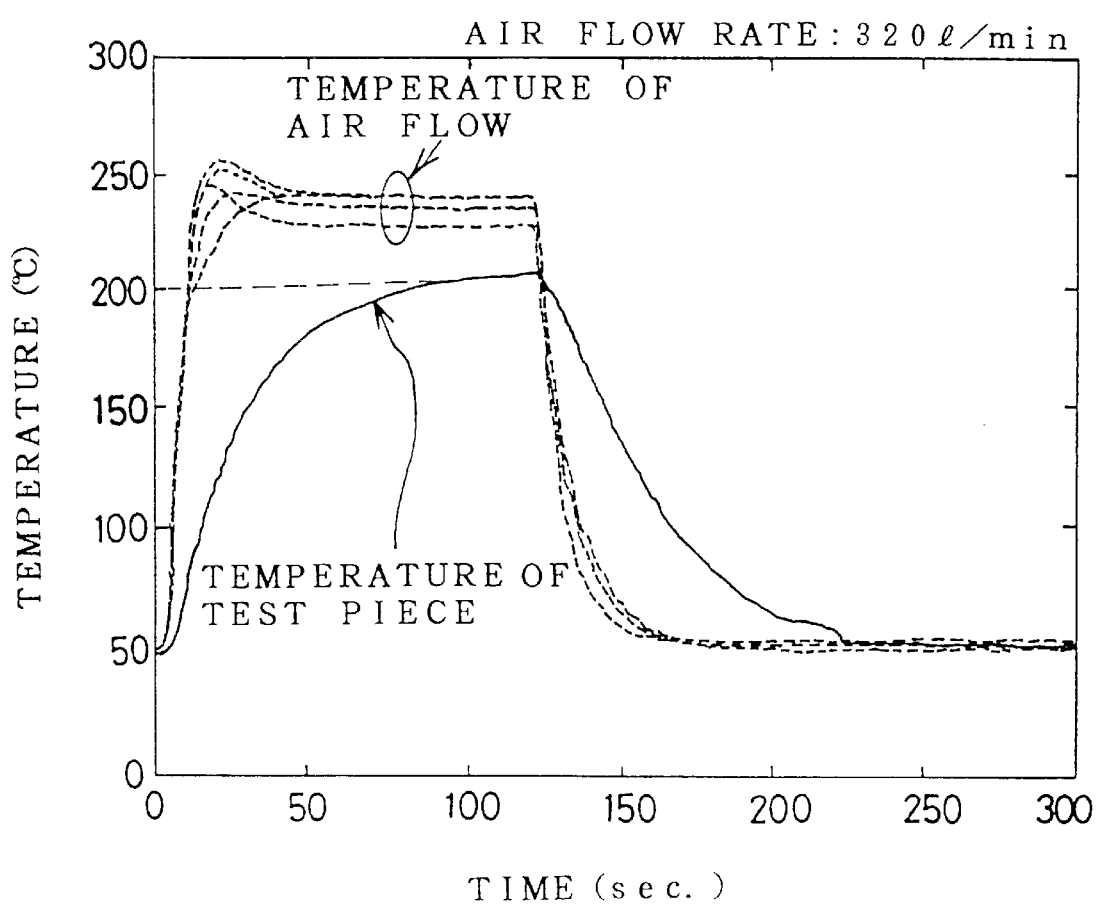
FIG. 12 is the time chart showing the temperature of each part as the result of test No. 1.

As a result, in a thermal cycle (300 sec) after several cycles, as shown in FIG. 12, the temperature of the middle portion of the test piece 40 converged precisely to a certain target temperature (200° C.). On the other hand, the temperature of each of the air flow( from the nozzles of the air ducts 1, 2) shows some overshoot in the beginning of heating, so it is recognized that the test unit 4 was heated up swiftly.

FIG. 12 also shows clearly that the temperature of the test piece 40 smoothly and asymptotically comes to a certain constant value, and that the thermal fatigue test can be performed in a short time such as 5 minutes (300 seconds) per cycle. Besides, the temperatures of the air flows are regulated almost constantly, and the temperatures of all air ducts 1, 2 are even enough. The airflow temperatures as shown by the dashed line cools drastically at about 120 seconds into the cycle and falls at least 50° C. within the next 10 seconds. For that reason, the whole test unit 4 is uniformly heated and cooled, and it was made sure that highly precise thermal fatigue test can be performed by the apparatus and the method for thermal fatigue test of the embodiment.

(5) Testing Result of the Embodiment No. 2

Some conditions were changed in this case, i.e., the pressure of the compressed air A was set constantly at 4 kg/cm², and the temperature of the air flow was constantly at about 300° C. or at the temperature of the compressed air A. No feedback control was performed in this case with the intention of checking the time necessary for heating and cooling by the hardware itself of the embodiment.

Figure 13:
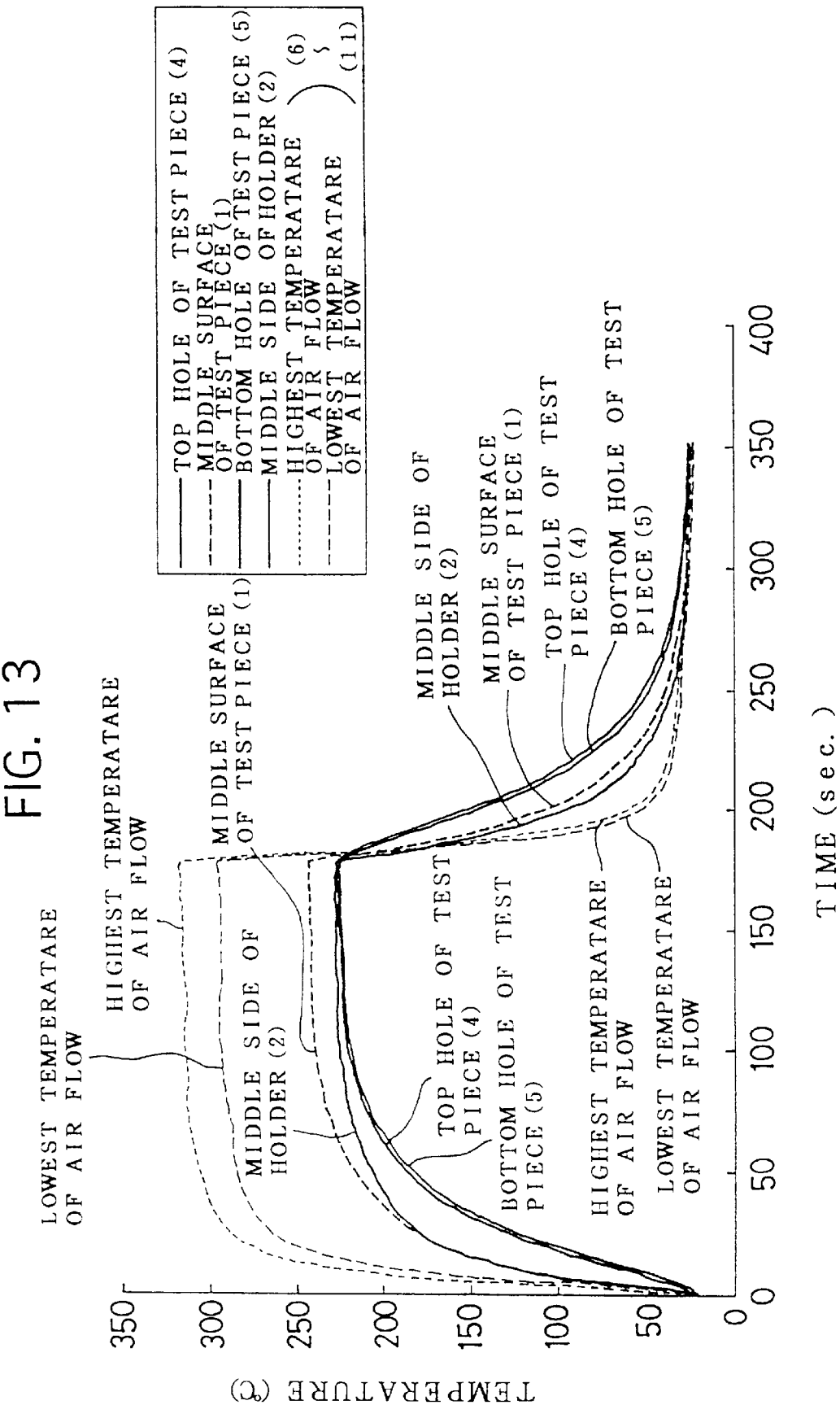
FIG. 13 is the time chart showing the temperature of each part as the result of test No. 2.

As a result, a time chart was obtained as shown in FIG. 13. FIG. 13 shows that the temperature distribution or the temperature of the middle portion of the test piece 40 ( i.e. the portion to be tested, see FIG. 7) had risen up in 100 seconds or so from the beginning of heating, and has shifted to stable state from 150 seconds or so. That is to say, the temperature (1) was rising up and falling down ahead of the temperatures (4), (5) in the holes at the upper and lower portions of the test piece, and got to be almost stable from 120–150 seconds or so. The airflow temperature, shown in dashed lines, falls drastically at about 180 seconds into the cycle and drops at least 50° C. within 10 seconds.

The result mentioned above shows that the temperatures of the test piece 40 and the holders 41, 42 can be kept stable constantly by keeping the temperatures (6)–(11) of the air flow from the air ducts 1, 2. It was also made clear that relatively swift control of the temperature can be performed, because the temperature of every portion of the test unit 4 comes to be stable in 120 seconds or so in heating and in cooling within the range from the room temperature to 250° C.

(6) Effectiveness of the Embodiment

As mentioned above, it was made clear that the apparatus and the method for thermal fatigue test of the preferred embodiment makes it possible to perform thermal fatigue test without any difficulty using a small, simple and inexpensive apparatus. Furthermore, the thermal fatigue test can be performed within a short interval such as a half cycle of 120 seconds or so, and makes it possible to produce a big reduction in testing time necessary for thermal fatigue test.

3. Modified Versions of the Embodiment (1) The First Modified Version of the Embodiment It is possible to modify the control law or algorithm which was shown in the above-mentioned two formulas by using the target temperature of the test piece 40 and the holders 41, 42 as the target temperature SV.

If the temperature control is performed according to this control law, more swift and precise thermal control can be effectively performed because the temperature (1) of the middle portion of the test piece 40 is directly taken account of the control as a target temperature.

(2) The Second Modified Version of the Embodiment

Thermal fatigue test can be performed with the apparatus of the embodiment by controlling the temperature and the strain of the test piece 40 independently.

That is to say, first of all, the temperature (1) of the middle portion of the test piece 40 is to be set as the target temperature SV, and the temperatures (8)–(11) of the air flow from the air ducts 1 are regulated to control the temperature (1) of the middle portion of the test piece 40 to certain desired temperature. Then, the temperatures (6), (7) of the air flow from the air ducts 2 are regulated to control the strain caused in the test piece 40 estimated by the temperature and the strain of the test piece 40 to certain desired stain. Even though it is described step by step to help understanding as mentioned above, the control of the air ducts 1 and 2 should be performed simultaneously to obtain swift response of the thermal control.

The thermal control mentioned above would bring out an additional effectiveness that the temperature and the stress of the test piece 40 can be controlled independently using the apparatus for testing thermal fatigue resistance of the embodiment, so that thermal fatigue test on desired conditions can be performed effectively.

(3) The Third Modified Version of the Embodiment

In the embodiment mentioned above, the electric heaters 11, 21 were heating wires in the shape of coils fixed inside of the air ducts 1, 2. But other kinds of heaters can be fixed in the air ducts 1, 2 instead of the electric heaters 11, 21. For example, ceramic heaters can be used as the electric heater. Any kinds of heaters including or not including electric heaters can be used substantially only if the heat output of the heater is controllable. In the embodiment, however, electric heating wires are used because of inexpensiveness, easy controllability and quick response.

(4) The Fourth Modified Version of the Embodiment

Though the flow rate of the compressed air A was fixed to be constant and the thermal control was performed by controlling heat output of the electric heaters 11, 21 in the embodiment, the thermal control of the air flow can also be performed by regulating the flow rate of the compressed air A with fixed heat output of the electric heaters 11, 21.

In this modified version, the flow rate can be regulated independently by controlling motorized throttle valves inserted to the air hoses 3, so that hot air flow of relatively low temperature is blown from the air ducts with high flow rate, and hot air flow of relatively high temperature is blown from the other air ducts with low flow rate. The throttle valves are not always necessary for each air duct. For example, one throttle valve might be placed for the air ducts 1 and another throttle valve for the air ducts 2. In addition, on/off control is enough for the control of the electric heaters 11, 21.

Thermal fatigue test almost similar to the embodiment mentioned above can be performed by the modified version.

In case both of the air flow rate from the air ducts 1, 2 and the heat output of the electric heaters 11, 21 are controlled, more precise thermal fatigue resistance test can be performed.

(5) The Fifth Modified Version of the Embodiment

Though the thermocouples were used as temperature sensors in the embodiment, they can be replaced with other kinds of thermosensors. For example, a heat ray camera (an infrared image sensor) can be used (instead or additionally).

Use of the infrared camera would make it possible to monitor the temperature of every part of the test unit 4 in real time, i.e., thermal observation at a multipoint can be performed. For that reason, that effectively makes it easier to obtain certain desired distribution or gradient of the temperature on the test piece 40 by controlling the air flow temperature from the plural air ducts individually. Further, test engineers can directly understand the distribution of the temperature by showing the thermoimage on the display. Moreover, labor cost is effectively reduced because no thermosensor is to be fixed on the test piece 40.

(6) The Sixth Modified Version of the Embodiment

PID feedback control law was used as the basic control law in the embodiment mentioned above. However, it is possible to introduce other control laws. For example, fuzzy control law can be introduced for the temperature control law.

In this version, fuzzy control system can be constructed by setting the membership functions appropriately based on experience knowledge of the test engineer, wherein the inputs are the measured temperature signals S1 and the outputs are the control signals S2 which control the applied voltage Vout for the electric heaters 11, 21. A control system with desired characteristics can be built up by coordinating the membership functions in some test run. Use of the fuzzy control would be able to eliminate the trouble of divergence (instability) of the control which often occurs in linear feedback loop system with excessively high gain, and would make it possible to perform temperature control with better response.

(7) The Seventh Modified Version of the Embodiment

The inventors have confirmed that LSI, condensers, semi-conductor tips, and electronic board equipped with these electronic elements can be tested in the thermal fatigue test (thermal cycle test) with the apparatus and by the method for testing mentioned above.

The presently disclosed embodiment and its modified versions are thereof in all respect to be illustrative, and not restrictive. The scope of the invention is indicated by the appended claims, rather than the foregoing description, and all changes that come within the meaning and range of equivalence thereof are intended to be embraced therein.

What is claimed is:

1. A method for testing thermal fatigue resistance, comprising the step of blowing a hot gas flow and a cold gas flow alternately to form a gas flow from at least two nozzles to at least two points on a test unit from at least two directions while controlling the temperature of said hot and cold gas flows individually, thereby giving thermal cycles to said test unit, wherein said hot gas flow is heated up to a constant temperature by directly heating said gas flow due to a heating means provided in a gas duct, said cold gas flow is cooled at a cooling rate of not less than 50° C. within 10 seconds by merely lowering an output of said heating means provided in said gas duct, at least one of a temperature of a certain point of said test unit and a temperature of said gas flow near said nozzle is measured, and temperature control of said gas flow is performed based on the result of the measurement.

2. The method of claim 1, wherein a gas of the gas flow is one selected from the group consisting of air, nitrogen gas and inert gas.

3. The method of claim 1, wherein said hot gas flow and cold gas flow are blown alternatively according to the following algorithm;

$$SV(1)=SVO$$

$$SV(i)=SV(i-1)+Etp(i-1)$$

wherein,

SV(i): target temperature of the gas flow in i-th cycle

SVO: initial target temperature of the gas flow

Etp (i−1): temperature deviation of the test unit in (i−1)th cycle,

Etp(i−1)=SVtp−PVtp(i−1)

Svtp: target temperature of the test unit

PVtp(i−1): measured temperature of the test unit.

4. The method of claim 1, wherein said heating means if an electrical heating means of which an output is controlled electrically, and said output is forcibly kept to an appropriate constant value for a certain duration at a beginning of heating and at a beginning of cooling in the thermal fatigue test and controlled by feedback control after the respective duration.

5. The method of claim 1, wherein said heating means is an electrical heating means of which an output is controlled electrically, said temperature control is a feedback control by which the output of said electrical heating means is controlled, and said feedback control is performed according to the following algorithm:

$$Vout=\{K \cdot Th(t)\}^\beta$$

wherein,

Vout: heater control signal (voltage or current)

t: time β: a constant index

Th(t): heater control value (temperature) based on deviation of controlled temperature of the gas flow by feedback control K: a predetermined constant.

6. The method of claim 5, wherein said feedback control is a PID feedback control, and Th (t) is obtained from the following algorithm:

$$Th(t)=100/PB \cdot \{e(t)+1/TI \cdot \int edt - TD \cdot de(t)/dt\}$$

wherein,

PB: proportional band (%)

TI: integration time

TD: differentiation time e(t): deviation of controlled temperature of the gas flow, e(t): SV−PT (t)

SV: target temperature of the gas flow

PV(t): measured temperature of the gas flow.

7. A method according to claim 1, wherein said heating means is provided at an end of said gas duct adjacent one of the nozzle.

8. A method for testing thermal fatigue resistance, comprising the step of blowing a hot gas flow and a cold gas flow alternately to form a gas flow from at least two nozzles to at least two points on a test unit from at least two directions while controlling the temperature of said hot and cold gas flows individually, thereby giving thermal cycles to said test unit, wherein said hot gas flow is heated up to a constant temperature by a heating means, said cold gas flow is cooled to a constant temperature by one of air cooling by merely lowering an output of said heating means and auxiliary heating by said heating means, at least one of a temperature of a certain point of said test unit and a temperature of said gas flow near one of said nozzles is measured, and temperature control of said gas flow is performed based on the result of the measurement.

9. The method of claim 8, wherein said hot gas flow and cold gas flow are blown alternatively according to the following algorithm:

$$SV(1)=SV0$$

$$SV(i)=SV(i-1)+Etp(i-1)$$

wherein,

SV(i): target temperature of the gas flow in i-th cycle
SV0: initial target temperature of the same
Etp (i−1): temperature deviation of the test unit in (i−1)th cycle,
Etp(i−1)=SVtp−PVtp(i−1)
SVtp: target temperature of the test unit
PVtp (i−1): measured temperature of the test unit.

10. The method of claim 8, wherein said heating means is an electrical heating means of which an output is controlled electrically, and said output is forcibly kept to an appropriate constant value for a certain duration at a beginning of heating and at a beginning of cooling in the thermal fatigue test and controlled by feedback control after the respective duration.

11. The method of claim 8, wherein said heating means is an electrical heating means of which an output is controlled electrically, said temperature control is a feedback control by which the output of said electrical heating means is controlled, and said feedback control is performed according to the following algorithm:

$$Vout=\{K \cdot Th(t)\}^\beta$$

wherein,

Vout: heater control signal (voltage or current)
t: time β: a constant index
Th(t): heater control value (temperature) based on deviation of controlled temperature of the gas flow by feedback control
K: a predetermined constant.

12. The method of claim 11, wherein said feedback control is a PID feedback control, and
Th(t) is obtained from the following algorithm:

$$Th(t)=100/PB \cdot \{e(t)+1/TI \cdot \int edt - TD \cdot de(t)/dt\}$$

wherein,

PB: proportional band (%)
TI: integration time
TD: differentiation time
e(t): deviation of controlled temperature of the gas flow,
e(t)=SV−PT (t)

SV: target temperature of the gas flow
PV(t): measured temperature of the gas flow.

13. The method of claim 8 wherein said test unit comprises a test piece, and holders which are made of a material with thermal expansion coefficient different from the thermal expansion coefficient of the test piece, the test piece is fixed to the holders such that thermal expansion of the test piece is restricted by the holders, a gas of the gas flow is one selected from the group consisting of air, nitrogen gas and inert gas.

14. A method according to claim 8, wherein said heating means is provided at an end of a gas duct adjacent one of nozzles.

15. A method for testing thermal fatigue resistance, comprising the step of blowing a hot gas flow and a cold gas flow alternately to form a gas flow from at least two nozzles to at least one point on a test unit while controlling the temperature of said hot and cold gas flows individually, thereby giving thermal cycles to said test unit, wherein said hot gas flow is heated up to a constant temperature by a heating means, said cold gas flow is cooled to a constant temperature by one of air cooling and auxiliary heating by said heating means, at least one of a temperature of a certain point of said test unit and a temperature of said gas flow near one of said nozzles is measured, temperature control of said gas flow is performed based on the result of the measurement, said test unit comprises a test piece, and holders which are made of a material with thermal expansion coefficient different from the thermal expansion coefficient of the test piece, the test piece is fixed to the holders such that thermal expansion of the test piece is restricted by the holders, said heating means is an electrical heating means of which the output is controlled electrically, said temperature control is PID feedback control by which the output of said electrical heating means is controlled, and said PID feedback control is performed according to the following algorithm:

$$Vout=\{K \cdot Th(t)\}^\beta$$

$$Th(t)=100/PB \cdot \{e(t)+1/TI \cdot \int edt - TD \cdot de(t)/dt\}$$

wherein,

Vout: heater control signal (voltage or current)
t: time β: a constant index
Th(t): heater control value (temperature)
PB: proportional band (%)
TI: Integration time
TD: differentiation time
e(t): deviation of controlled temperature of the gas flow
e(t)=SV−PT (t)
SV: target temperature of the gas glow
PV(t): measured temperature of the gas flow
K: a predetermined constant.

16. A method for testing thermal fatigue resistance, comprising the step of blowing a hot gas flow and a cold gas flow alternately to form a gas flow from at least two nozzles to at least one point on a test unit while controlling the temperature of said hot and cold gas flows individually, thereby giving thermal cycles to said test unit, wherein said hot gas flow is heated up to a constant temperature by a heating means, said cold gas flow is cooled to a constant temperature by one of air cooling and auxiliary heating by said heating means, at least one of a temperature of a certain point of said test unit and a temperature of said gas flow near one said nozzles is measured, temperature control of said gas flow is performed based on the result of the measurement, said test unit comprises a test piece, and holders which are made of a material with thermal expansion coefficient different from the thermal expansion coefficient of the test piece, the test piece is fixed to the holders such that thermal expansion of the test piece is restricted by the holders, said hot gas flow and cold gas flow are blown alternatively according to the following algorithm:

$$SV(1) = SV0$$

$$SV(i) = SV(i-1) + Etp(i-1)$$

wherein,

SV(i): target temperature of the gas flow in i-th cycle

SV0: initial target temperature of the gas flow

Etp (i−1): temperature deviation of the test unit in (i−1)th cycle, etp(i−1)=SVtp−PVt(i−1)

SVtp: target temperature of the test unit

PVtp (i−1): measured temperature of the test unit.

\* \* \* \* \*